(12) United States Patent
Lafferty

(10) Patent No.: US 6,798,520 B2
(45) Date of Patent: Sep. 28, 2004

(54) METHOD FOR INTENSIFYING THE OPTICAL DETECTION OF SAMPLES THAT ARE HELD IN SOLUTION IN THE THROUGH-HOLE WELLS OF A HOLDING TRAY

(75) Inventor: William Michael Lafferty, Encinitas, CA (US)

(73) Assignee: Diversa Corporation, San Diego, CA (US)

(*) Notice: Subject to any disclaimer, the term of this patent is extended or adjusted under 35 U.S.C. 154(b) by 108 days.

(21) Appl. No.: 10/103,977

(22) Filed: Mar. 22, 2002

(65) Prior Publication Data
US 2003/0179378 A1 Sep. 25, 2003

(51) Int. Cl.$^7$ .............................................. G01N 21/00
(52) U.S. Cl. ....................... 356/440; 356/246; 422/101; 422/104
(58) Field of Search ................................. 356/432–440, 356/244, 246; 436/174, 514; 422/101, 104

(56) References Cited

U.S. PATENT DOCUMENTS

| | | | |
|---|---|---|---|
| 4,299,796 A | | 11/1981 | Hogen Esch |
| 4,312,009 A | * | 1/1982 | Lange ........................ 347/51 |
| 4,682,891 A | | 7/1987 | de Macario |
| 4,704,255 A | | 11/1987 | Jolley |
| 4,710,031 A | | 12/1987 | Kelly |
| 4,735,778 A | | 4/1988 | Maruyama |
| 4,824,791 A | | 4/1989 | Ekholm |
| 5,213,505 A | | 5/1993 | Laipply |
| 5,262,128 A | | 11/1993 | Leighton et al. |
| 5,849,598 A | | 12/1998 | Wilson et al. |
| 6,027,873 A | | 2/2000 | Schellenberger |
| 6,071,748 A | * | 6/2000 | Modlin et al. .............. 436/174 |
| 6,306,578 B1 | | 10/2001 | Schellenberger |
| 6,555,389 B1 | * | 4/2003 | Ullman et al. ............. 436/514 |
| 2002/0001546 A1 | | 1/2002 | Hunter et al. |
| 2002/0015994 A1 | | 2/2002 | Schellenberger et al. |

FOREIGN PATENT DOCUMENTS

| | | |
|---|---|---|
| WO | WO/99/34920 | 7/1999 |
| WO | WO 00/55327 | 9/2000 |
| WO | WO 02/16651 A2 | 2/2002 |

* cited by examiner

Primary Examiner—Hoa Q. Pham
(74) Attorney, Agent, or Firm—Nydegger & Associates

(57) ABSTRACT

A system and method for optically detecting samples held in a solution requires the use of a holding plate that has as many as one-thousand through-hole wells, or more. The solution is suspended in these through-hole wells under surface tension between opposed surfaces of the holding plate. A pneumatic pump is then engaged with the plate to establish a differential pressure ($\Delta p$) between the upper and lower surfaces of the solution that is equal to approximately two tenths of a pound per square inch (0.2 psi). The result is the formation of a convex meniscus on a surface of the solution that causes light passing into the solution to converge and concentrate. This concentration of light, in turn, facilitates optical detection of samples in the solution.

20 Claims, 1 Drawing Sheet

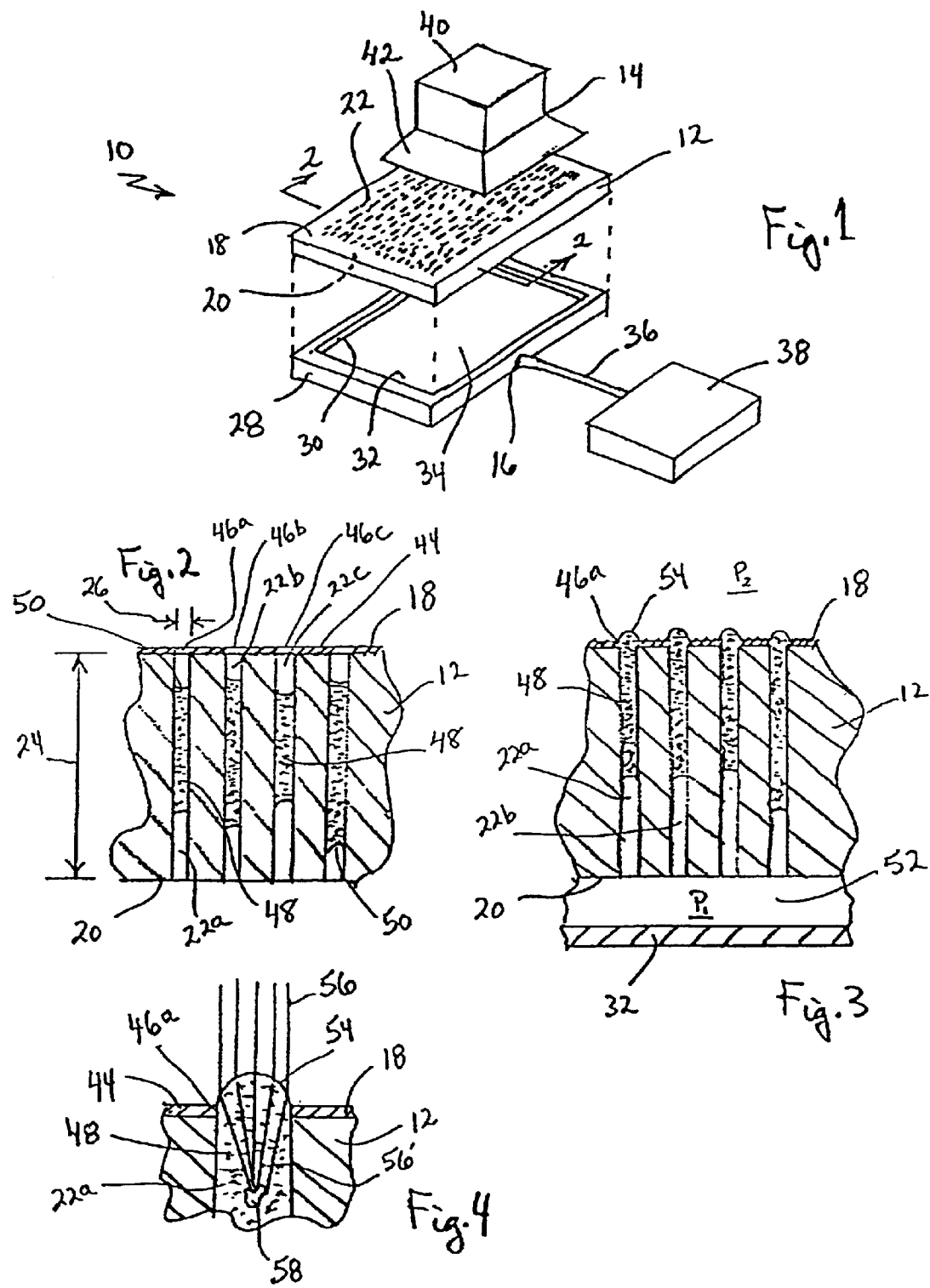

METHOD FOR INTENSIFYING THE OPTICAL DETECTION OF SAMPLES THAT ARE HELD IN SOLUTION IN THE THROUGH-HOLE WELLS OF A HOLDING TRAY

FIELD OF THE INVENTION

The present invention pertains generally to plates for holding assays. More particularly, the present invention pertains to holding plates and methods for their use that facilitate the observation, detection and retrieval of specimen samples as they are being held on the plate in a fluid solution. The present invention is particularly, but not exclusively, useful for altering the optical characteristics of fluid solutions, as they are being suspended in the through-hole wells of holding plates, for the purpose of detecting specimen samples that are being held in the solution.

BACKGROUND OF THE INVENTION

Capillary action is a phenomenon associated with surface tension that occurs in fine bore tubes or channels. Typically, such tubes or channels are referred to as capillary tubes, and it is well known that the elevation to which a liquid will rise in a capillary tube can be mathematically determined. It happens that this phenomenon has many applications, one of which is that it can be used to fill the through-hole wells of a holding plate. More specifically. it has been shown that through-hole wells having aspect ratios greater than about 5:1, and inner diameters that are less than approximately five hundred microns will exhibit the capillary phenomenon.

It is a consequence of capillary action that the liquid in a fine bore tube, such as a through-hole well in a holding plate, will form a meniscus. This meniscus, which is a departure from a flat surface where a liquid meets a solid, is caused by surface tension and is easily observable. Importantly, a meniscus will refract light that is passing into or out of the liquid in a manner that is dependent on its particular shape. In the case of aqueous solutions, and most other light transmitting fluids, the meniscus will be generally concave. Accordingly, the meniscus will optically function as a concave lens that causes light entering the liquid to diverge.

One important capability of any assay holding plate is that the specimen samples that are being held in the plate are detectable and observable. in the case of holding plates that have capillary tube-like, through-hole wells, there are optical issues that need to be resolved when light is being used for these purposes. As indicated above, as light enters through a concave meniscus into a sample solution, the concave meniscus will cause the light to diverge. If the walls of through-hole wells in a holding plate are light absorptive, as may be desired, diverging light will be absorbed by the walls. This fact can significantly reduce the amount of light that is available for interaction with a specimen sample in the solution. Under these circumstances, detection of the sample is more difficult.

in light of the above, it is an object of the present invention to provide a system and method for detecting specimen samples that are being suspended in a liquid solution under surface tension in a holding plate. Another object of the present invention is to provide a system and method that creates a convex or flat meniscus on a liquid solution which will cause light entering the solution to converge and concentrate, to thereby facilitate the detection of any specimen samples that are being held in the solution. Still another object of the present invention is to provide a system and method for detecting specimen samples suspended in a solution in a capillary tube that is easy to use, simple to manufacture and comparatively cost effective.

SUMMARY OF THE PREFERRED EMBODIMENTS

A system for optically detecting samples in a solution, while the solution is being held in a capillary tube under surface tension, includes a holding plate that has opposed first and second surfaces. A plurality of substantially parallel through-hole wells (i.e. capillary tubes) extend through the holding plate between these opposed surfaces. As envisioned for the present invention, the holding plate can have more than one thousand such through-hole wells, and each through-hole well will have an aspect ratio that is greater than about 5:1. Also, each through-hole well will have an inner diameter that is less than approximately five hundred microns.

A pneumatic pump, or some similar type device well known in the pertinent art, is engageable with the holding plate to establish a differential pressure ($\Delta p$) between the first and second surfaces of the holding plate. This differential pressure ($\Delta p$) will, of course, also affect any liquid solutions that are being held in respective through-hole wells of the holding plate. The result of this is that the differential pressure ($\Delta p$) tends to force the liquid solutions from their respective through-hole wells. in this case, the force reacting against the differential pressure ($\Delta p$) will be primarily the result of surface tension on the liquid solution. Mathematically, a surface tension calculation for a 200 $\mu$m capillary can be made using the expression:

$$P=4\sigma/d$$

where
P=pressure due to meniscus
$\sigma$=water surface tension=0.0727 N/m
d=capillary diameter=200 $\mu$m
the result will be $$P=(4\times0.0727)/(200\times10^{-6})=1454 \text{ N/m}^2 \approx 0.2 \text{ psi.}$$

Thus, by properly controlling the differential pressure ($\Delta p$) to less than approximately two tenths of a pound per square inch (0.2 psi), the liquid solution can be moved through the through-hole well, but not forced from the well. Instead, as the fluid solution attempts to leave the through-hole well, it will bulge at the exit to form a convex meniscus. This effect can be further enhanced by coating the surface that surrounds the entrance/exit of the through-hole well with a hydrophobic coating, such as Teflon®.

As intended for the present invention, the convex meniscuses that are created at the entrances, or exits, of respective through-hole wells on a surface of the plate are used to optical advantage. Specifically, when lighting devices are used to detect samples held in the through-hole wells of a holding plate, these convex meniscuses will cause light that passes into the solution through the meniscus to converge, rather than diverge. The resultant concentration of light in the solution can then be used to facilitate optical detection of samples in the solution. It will be appreciated by the skilled artisan that this result can be at least partially achieved merely by moving the bolus of fluid closer to the exit/entrance of a through-hole well.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a perspective schematic view of the system of the present invention;

FIG. 2 is a cross-sectional view of a portion of the holding plate as seen along the line 2-2 in FIG. 1;

FIG. 3 is a cross-sectional view of the holding plate as seen in FIG. 2 with a differential pressure ($\Delta p$) being applied; and FIG. 4 is an enlarged view of a convex meniscus as it is formed at the entrance/exit of a through-hole well in a holding plate, as it would be viewed in FIG. 3.

DESCRIPTION OF THE PREFERRED EMBODIMENT

Referring initially to FIG. 1, a system in accordance with the present invention for optically detecting samples held in a fluid solution is shown and generally designated 10. As shown, the system 10 includes a holding plate 12, an optical detector 14 for viewing the plate 12, and a pneumatic device 16 for imposing a pressure differential ($\Delta p$) on the holding plate 12. In the operation of the system 10, the pneumatic device 16 generates the pressure differential $\Delta p$ to establish a configuration for the fluid solution that enhances the ability of the optical detector 14 to detect specimen samples that are being held in solution.

With specific reference to the holding plate 12, it is shown in FIG. 1 that this holding plate 12 has a first surface 18 and a second surface 20. These surfaces 18 and 20 are both substantially flat, and they are generally parallel to each other. Importantly, the plate 12 also includes a plurality of through-hole wells 22 that are substantially parallel to each other, and that extend through the plate 12 between the surfaces 18 and 20. As perhaps best appreciated with reference to FIG. 2, each of the through-hole wells 22 in plate 12 (of which the through-hole wells 22a, 22b and 22c are only exemplary) have a length 24 and an inner diameter 26. For the present invention, it is contemplated that the inner diameter 26 will be approximately equal to, or less than, about five hundred microns (500 $\mu$m). Further, it is contemplated that each through-hole well 22 will have an aspect ratio (i.e. the ratio of length 24 to diameter 26) that will be equal to or greater than about 5:1. In any event, it is essentially important that the through-hole wells 22 effectively exhibit capillary action.

Still referring to FIG. 1, it will be seen that the pneumatic device 16 of system 10 includes a tray 28. As shown, the tray 28 is formed with a wall 30, and it has a bottom 32 which, together with the wall 30, creates a cavity 34. Further, a tube 36 is attached to the tray 28. Specifically, the tube 36 connects the cavity 34 of tray 28 in fluid communication with an air pump 38. It is also seen in FIG. 1 that the optical detector 14 of system 10 includes a camera 40 and a light source 42. It is to be appreciated by the skilled artisan that any light detection device (the camera 40 is only exemplary) can be used for the purposes of the present invention. Also, it is to be appreciated that, depending on the particular application of the system 10, the light source 42 can selectively generate visible or invisible light, as well as collimated light, or monochromatic light of a particular wavelength.

Referring now to FIG. 2 it will be seen that the surface 18 of plate 12 can be coated with a hydrophobic coating 44. Though not shown, it is to be appreciated that the surface 20 could be similarly coated. Importantly, for purposes to be subsequently disclosed, the coating 44 is shown to surround the respective openings 46 of the various through-hole wells 22. In FIG. 2 it is also shown that individual portions of a solution 48 are suspended in respective through-hole wells 22. As implied above, the solution 48 is introduced into the through-hole wells 22 by capillary action, and is suspended therein under the influence of surface tension on the solution 48. Accordingly, in most instances, the solution 48 will be of a fluid type that will create a concave meniscus 50 as it is suspended in the through-hole well 22. It will also be appreciated that the hydrophobic coating 44 will inhibit transfer of fluid from one through-hole well 22 to another.

In the operation of the system 10 of the present invention, the tray 28 of pneumatic device 16 is engaged with the holding plate 12. More specifically, as best appreciated with reference to FIG. 3, this engagement converts the cavity 34 of tray 28 into an air-tight chamber 52 that is located between the bottom 32 of the tray 28 and the second surface 20 of the holding plate 12. With this configuration, an activation of the air pump 38 can create a pressure, $p_1$, in the chamber 52 that is greater than the ambient pressure, $p_2$, on the first surface 18 of holding plate 12. Consequently, a pressure differential $\Delta p$ is created ($\Delta p = p_1 - p_2$) that tends to force the solution 48 from through-hole wells 22a–c out of the respective openings 46a–c. It will be appreciated, however, that rather than creating an overpressure as just described, a suction device (not shown) could as easily be engaged with the first surface 18 to accomplish the same result. Also, air pump 38 could be operated to create a vacuum in chamber 52. In this case, the solution 48 would be forced toward the surface 20 of holding plate 12. Nevertheless, in any case, the desired result is the creation of a convex meniscus 54 on the solution 48 at the respective opening 46 of each through-hole well 22.

The optical functionality of a convex meniscus 54 when generated for purposes of the present invention is, perhaps, best appreciated by reference to FIG. 4. There, it can be seen that due to the shape of the convex meniscus 54, light rays 56 will be refracted in a predictable way as they are incident on the meniscus 54 of the solution 48. Specifically, as light rays 56 pass from air into the solution 48, they will be refracted in a converging manner as shown in FIG. 4 (the light ray 56' is exemplary). As intended for the present invention, this converging effect helps focus more light into the respective through-hole well 22 for enhanced illumination of particles 58 that may be suspended in the solution 48.

While the particular Method for Intensifying the Optical Detection of Samples That Are Held in Solution in the Through-Hole Wells of a Holding Tray as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for optically detecting samples held in a solution which comprises:

a holding plate having a first surface and a second surface with a plurality of through-hole wells therethrough; and a pneumatic means engageable with said plate for creating a differential pressure ($\Delta p$) between said first and second surfaces of said holding plate to force said solution in said through-hole wells to form a convex meniscus at said first surface of said plate to project outwardly from said first surface, and cause light passing into said solution through said convex meniscus to converge and concentrate in said solution to facilitate optical detection of said samples in said solution.

2. A system as recited in claim 1 wherein said pneumatic means is an air pump.

3. A system as recited in claim 2 wherein said differential pressure (Δp) is approximately two tenths of a pound per square inch (0.2 psi).

4. A system as recited in claim 1 further comprising an optical means for directing light the convex meniscus.

5. A system as recited in claim 1 further comprising a hydrophobic coating on said first surface to enhance formation of the convex meniscus.

6. A system as recited in claim 1 wherein each of said through-hole wells in said holding plate has an aspect ratio greater than 5:1 and an inner diameter less than approximately five hundred microns.

7. A system for optically detecting samples held in a solution which comprises:
 a mechanical means for suspending said solution under surface tension, said suspended solution having an upper surface exposed to ambient conditions and a lower surface exposed to said same ambient conditions; and
 a pneumatic means engageable with said mechanical means for forming one said surface of said solution with a convex meniscus to project outwardly from said mechanical means to cause light passing into said solution through said convex meniscus to converge and concentrate in said solution to facilitate optical detection of said samples in said solution.

8. A system as recited in claim 7 wherein said mechanical means is a holding plate having a first surface and a second surface with a plurality of through-hole wells extending therebetween, and wherein said solution is suspended in respective said through-hole wells between said first and second surfaces of said holding plate.

9. A system as recited in claim 8 wherein each of said through-hole wells in said holding plate has an aspect ratio greater than 5:1 and an inner diameter less than approximately five hundred microns.

10. A system as recited in claim 8 wherein said holding plate has more than one thousand said through-hole wells.

11. A system as recited in claim 8 wherein said pneumatic means is an air pump for creating a differential pressure (Δp) between said upper and lower surfaces of said solution.

12. A system as recited in claim 11 wherein said differential pressure (Δp) is approximately two tenths of a pound per square inch (0.2 psi).

13. A system as recited in claim 8 further comprising an optical means for directing light through the convex meniscus.

14. A system as recited in claim 8 further comprising a hydrophobic coating on said first surface to enhance formation of the convex meniscus.

15. A method for optically detecting samples held in a solution which comprises the steps of:
 providing a holding plate having a first surface and a second surface with a plurality of through-hole wells therethrough for suspending said solution under surface tension in respective said through-hole wells between said first and second surfaces of said holding plate, said suspended solution having an upper surface exposed to ambient conditions and a lower surface exposed to said same ambient conditions;
 engaging a pneumatic means with said plate to project outwardly from said first surface and form one said surface of said solution with a convex meniscus; and
 directing light through said convex meniscus to cause light passing into said solution therethrough to converge and concentrate in said solution to facilitate optical detection of said samples in said solution.

16. A method as recited in claim 15 wherein each of said through-hole wells in said holding plate has an aspect ratio greater than 5:1 and an inner diameter less than approximately five hundred microns, and wherein said holding plate has more than one thousand said through-hole wells.

17. A method as recited in claim 15 wherein said pneumatic means is an air pump for creating a differential pressure (Δp) between said upper and lower surfaces of said solution.

18. A method as recited in claim 17 wherein said differential pressure (Δp) is approximately two tenths of a pound per square inch (0.2 psi).

19. A method as recited in claim 15 wherein said directing step is accomplished using an optical means.

20. A method as recited in claim 15 further comprising the step of coating a hydrophobic on said first surface of said holding plate to enhance formation of the convex meniscus.

* * * * *

UNITED STATES PATENT AND TRADEMARK OFFICE
CERTIFICATE OF CORRECTION

PATENT NO. : 6,798,520 B2
DATED : September 28, 2004
INVENTOR(S) : Lafferty

It is certified that error appears in the above-identified patent and that said Letters Patent is hereby corrected as shown below:

Column 1,
Line 46, delete "observable in" and insert -- observable. In --.
Line 58, delete "in" and insert -- In --.

Column 2,
Line 27, delete "wells in" and insert -- wells. In --.

Column 5,
Line 12, delete "light the" and insert -- light through the --.

Signed and Sealed this

Twenty-third Day of May, 2006

JON W. DUDAS
*Director of the United States Patent and Trademark Office*